US008703948B2

(12) United States Patent
Mehrman et al.

(10) Patent No.: US 8,703,948 B2
(45) Date of Patent: Apr. 22, 2014

(54) SALTS OF 3-(3-AMINO-2-(R)-HYDROXY-PROPYL)-1-(4-FLUORO-PHENYL)-8-(8-METHYL-NAPHTHALEN-1-YLMETHYL)-1,3,8-TRIAZA-SPIRO[4.5]DECAN-4-ONE

(75) Inventors: Steven J. Mehrman, Quakertown, PA (US); Armin Roessler, Tengen (DE); Roger Faessler, Stetten (CH); Frank J. Villani, Perkasie, PA (US); Jean Francois Alexandre Lucas, Diest (BE)

(73) Assignee: Janssen Pharmaceutica NV (BE)

( * ) Notice: Subject to any disclaimer, the term of this patent is extended or adjusted under 35 U.S.C. 154(b) by 1099 days.

(21) Appl. No.: 11/939,789

(22) Filed: Nov. 14, 2007

(65) Prior Publication Data

US 2008/0176882 A1    Jul. 24, 2008

Related U.S. Application Data

(60) Provisional application No. 60/861,378, filed on Nov. 28, 2006.

(51) Int. Cl.
*C07D 401/00* (2006.01)

(52) U.S. Cl.
USPC .......................................................... 546/18

(58) Field of Classification Search
USPC .......................................................... 546/18
See application file for complete search history.

(56) References Cited

U.S. PATENT DOCUMENTS

| | | | |
|---|---|---|---|
| 3,155,670 A | 11/1964 | Janssen | |
| 3,155,699 A | 11/1964 | Powers et al. | |
| 3,161,644 A | 12/1964 | Janssen et al. | |
| 3,238,216 A | 3/1966 | Adriaan | |
| 3,629,267 A | 12/1971 | Kaiser et al. | |
| 3,839,340 A | 10/1974 | Scharpf et al. | |
| 3,859,340 A | 1/1975 | Stiller et al. | |
| 4,020,072 A | 4/1977 | Hoehn et al. | |
| 4,329,363 A | 5/1982 | Dorn et al. | |
| 4,414,216 A | 11/1983 | Kawakita et al. | |
| 4,526,896 A | 7/1985 | Scherrer et al. | |
| 5,486,362 A | 1/1996 | Kitchell et al. | |
| 5,739,336 A | 4/1998 | Weinhardt et al. | |
| 6,043,366 A | 3/2000 | Adam et al. | |
| 6,060,482 A | 5/2000 | Heine et al. | |
| 6,071,925 A | 6/2000 | Adam et al. | |
| 6,113,527 A | 9/2000 | Adam et al. | |
| 6,172,076 B1 | 1/2001 | Embrey et al. | |
| 6,262,066 B1 | 7/2001 | Tulshian et al. | |
| 6,277,991 B1 | 8/2001 | Hohlweg et al. | |
| 6,465,478 B1 | 10/2002 | Ito et al. | |
| 6,777,421 B2 | 8/2004 | Jordan et al. | |
| 7,053,101 B2 | 5/2006 | Jordan et al. | |
| 7,081,463 B2 | 7/2006 | Battista et al. | |
| 7,192,964 B2 | 3/2007 | Hashimoto et al. | |
| 7,557,117 B2 | 7/2009 | Hashimoto et al. | |
| 7,582,649 B2 | 9/2009 | Battista et al. | |
| 2001/0011092 A1 | 8/2001 | Tulshian et al. | |
| 2003/0109538 A1 | 6/2003 | Carter et al. | |
| 2003/0109539 A1 | 6/2003 | Jordan et al. | |
| 2003/0158219 A1 | 8/2003 | Ito et al. | |
| 2004/0014955 A1* | 1/2004 | Zamudio et al. | 536/23.1 |
| 2004/0142955 A1* | 7/2004 | Battista et al. | 514/278 |
| 2005/0004154 A1 | 1/2005 | Jordan et al. | |
| 2005/0004363 A1 | 1/2005 | Hashimoto et al. | |
| 2008/0200492 A1 | 8/2008 | Vaidya | |

FOREIGN PATENT DOCUMENTS

| | | |
|---|---|---|
| EP | 0856514 B1 | 8/1998 |
| EP | 0921125 B1 | 6/1999 |
| EP | 0997464 B1 | 2/2005 |
| JP | 2000-128879 | 5/2000 |
| JP | 2000-169476 | 6/2000 |
| WO | WO 88/00190 | 1/1988 |
| WO | WO 95/07294 | 3/1995 |
| WO | WO 97/07212 | 2/1997 |
| WO | WO 97/07212 A1 | 2/1997 |
| WO | WO 97/36871 | 10/1997 |
| WO | WO 93/12789 | 7/1999 |
| WO | WO 99/59997 | 11/1999 |
| WO | WO 99/65494 | 12/1999 |
| WO | WO 00/06545 | 2/2000 |
| WO | WO 0015222 | 3/2000 |
| WO | WO 00/31037 | 6/2000 |
| WO | WO 01/07050 A1 | 2/2001 |
| WO | WO 01/36418 A1 | 5/2001 |
| WO | WO 01/38720 | 5/2001 |
| WO | WO 01/39723 A2 | 6/2001 |
| WO | WO 01/46192 | 6/2001 |
| WO | WO 01/94346 A1 | 12/2001 |
| WO | WO 01/96337 | 12/2001 |

(Continued)

OTHER PUBLICATIONS

Calo, G., et al. "Pharmacology of Nociceptin and Its Receptor: a Novel Therapeutic Target", British Journal of Pharmacology, 2000, vol. 129, pp. 1261-1291199.
Meunier, J., e al. "Isolation and Structure of the Endogenous Agonist of Opioid Receptor-Like $ORL_1$ Receptor", Letters to Nature, vol. 377, pp. 532-535.
U.S. Appl. No. 12/327,437, filed Dec. 3, 2008, Notice of Allowance, Date Jul. 10, 2013.
U.S. Appl. No. 12/327,437, filed Dec. 3, 2008, Notice of Allowance, Date Apr. 3, 2013.
U.S. Appl. No. 12/327,437, filed Dec. 3, 2008, Notice of Allowance, Date May 14, 2012.
U.S. Appl. No. 12/327,437, filed Dec. 3, 2008, Notice of Allowance, Date Sep. 6, 2010.
U.S. Appl. No. 12/030,911, filed Feb. 14, 2008, Examiner Interview and NOA Date Apr. 23, 2013.

(Continued)

*Primary Examiner* — Nizal Chandrakumar
(74) *Attorney, Agent, or Firm* — Michele G. Mangini

(57) ABSTRACT

The present invention is directed to salts of 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one, pharmaceutical compositions containing them and their use in the treatment of disorders and conditions modulated by NOP, for example depression, anxiety, alcohol abuse, etc. The present invention is further directed to process(es) for the preparation of 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one and its corresponding salts.

6 Claims, No Drawings

(56) References Cited

FOREIGN PATENT DOCUMENTS

| WO | WO 02/083673 A1 | 10/2002 |
|---|---|---|
| WO | WO 02/085355 A1 | 10/2002 |
| WO | WO 03/010168 A1 | 6/2003 |
| WO | WO 2004/022558 | 3/2004 |
| WO | WO 2004/022558 A | 3/2004 |
| WO | WO 2008/067177 | 6/2008 |
| WO | WO 2008/124209 | 10/2008 |
| WO | WO 2010/033451 | 3/2010 |

OTHER PUBLICATIONS

U.S. Appl. No. 12/030,911, filed Feb. 14, 2008, Notice of Appeal, Date Mar. 12, 2013.
U.S. Appl. No. 12/030/911, filed Feb. 14, 2008, OA Date Dec. 12, 2012.
U.S. Appl. No. 12/030,911, filed Feb. 14, 2008, OA Date Aug. 24, 2012.
Bignan G.C., et al., "Recent Advanced Towards the Discovery of ORL-1 Receptor Agonists and Antagonists," 14(4) Expert Opinion. Ther. Patents 357-388 (2005).
Zaveri, "Peptide and Nonpeptide Ligands for the Nociceptin/Orphanin FQ Receptor ORL1: Research Tools and Potential Therapeutic Agents," 73 Life Sciences 663-678 (2003).
Patani, et al, "Bioisosterism: A Rational Approach in Drug Design", Chem. R., 1996, pp. 3147-3176, vol. 96.
Cometta-Morini, et al., "Molecular Determinants of μ Receptor Recognition for the Fentanyl class of Compounds", Jan. 1992, pp. 185-196, vol. 41, No. 1.
Satyamurthy, et al., "3-(2'-[$^{18}$F]Fluoroethyl)spiperone, a Potent Dopamine Antagonist: Synthesis, Structural Analysis and in-vivo Utilization in Humans★", 1990, pp. 113-129, vol. 41, No. 2.
Wolf, et al, "Rational Development of Practical Catalysts for aromatic Carbon-Nitrogen Bond formation", Acc. Chem. Res., 1998, pp. 805-818, vol. 31.
Koster, et al., "Combined Pharmacological and Genetic Approach to Studying the Role of Orphanin FQ on Cognition" PNAS, pp. 10444-10449, vol. 96.
Janssen C. STN English Abstract DN 60:90893 BE633914 Dec. 1963.
What drugs are approved for Alzheimer Disease, Jul. 31, 2010, Fisher Center for Alzheimer Research Foundation.
Kiesewetter, D. et al., "Syntheses and D.sub.2 Receptor Affinities of Derivatives of Spiperone Containing Aliphatic Halogens" Appl. Radiat. Isot. 1986, 37(12), 1181-1188.
Chalon, S. et al "Iodoethylspiperone, a New Potential Agent for Exploration of Central Dopamine D.sub.2 Receptors: Synthesis and Preliminary in Vivo Study" Nucl. Med. Bio. 1990, 17(4), 389-395.
Meunier, Jean-Claude et al. "Isolation and structure of the endogenous agonist of opioid receptor-like ORL sub 1 receptor." Nature, 1995, 377, 532-535.
Rover S. et al., "High-Affinity, Non-Peptide Agonists for the ORL1 (Orphanin FQ/Nociceptin) Receptor" J. Med. Chem., 43, 1329-1338.
Acsády, L., et. al., "Nerve Growth Factor But Not Neurotrophin-3 is Synthesized by Hippocampal Gabaergic Neurons That Project to the Medial Septum." Neuroscience, vol. 98, No. 1, pp. 23-31.
Jenck, Francois et al., "A synthetic agonist at the orphanin FQ/nociceptin receptor ORL1: Anxiolytic profile in the rat," PNAS, Apr. 25, 2000, vol. 97, No. 9, pp. 4938-4953.
Calo, Girolamo, et al., Pharmacology of nociceptin and its receptor: a novel therapeutic target. Briti.J. of Pharm. 2000, 129, 1261-1283.
Poulain, R. et al., "From Hit to Lead. Combining Two Complementary Methods for Focused Library Design. Application to .mu. Opiate Ligands" J. Med. Chem. 2001, 44, 3378-3390.
Poulain, R. et al., "From Hit to Lead. Analyzing Structure—Profile Relationship" J.Med. Chem. 2001, 44, 3391-3401.
Ronzoni, Silvano et al., "Lead generation and lead optimization approaches in the discovery of selective, non-peptide ORL-1 receptor agonists and antagonists," Exp. Opin. Ther. Patents, 2001, (11) 4, pp. 525-546.

Thomsen, Chrisian et al., "(8-Napthalen-1-ylmethyl-4-oxo-1-phenyl-1,3,8-triaza-spiro[4,5]-dec-3-yl)-acetic acid methyl ester (NNC 63/0532) is a novel potent nociceptin receptor agonist,"British Journal of Pharmacology (2000) 131, 903-908.
Calo, G. et al., "Pharmacological Profile of Nociceptin/Orphanin FQ Receptors" Clinical and Experimental Pharmacology and Physiology; 2002, 29, 223-228.
Meunier, et al., "The potential therapeutic value of nociceptin receptor agonists and antagonists", Expect Opinion on Therapeutics Patents, 2000, pp. 371-388, vol. 10, (4).
Collier, et al., Br. J. Pharmacol., 1968, 32, 295.
Dirig, et al., J. Neurosci. Methods, 1997, 76, 183.
Dirig, et al., J. Pharmacol. Expt. Therap., 1998, 285, 1031.
Henderson G, et al., The orphan Opioid receptor and its endogenous ligand nociceptin/orphanin FQ:; Trends in Pharmacological Sciences, Elsevier Trends Journal, pp. 293-300, Aug. 1, 1997, vol. 18, No. 8, XP004085920; ISSN: 0165-6147, Cambridge, GB.
Higgins, et al., In European Forum of Neuroscience 2000, Brighton, U.K., Jun. 24-28, 2000, Poster 077.22.
Pellow et al., J. Neurosci Methods 14: 149-167, 1985.
Pulito, V.L. et al., 2000, J. Pharmacol. Exp. Ther. 294, 224-229.
Randall and Selitto, Arch. Int. Pharmacodyn., 1957, 4, 409.
Selway et al., Bioorganic & Medicinal vol. 4, No. 5 pp. 645-654 1996.
Thurkauf, A. et al., "1-Pheynl-3-(aminomethyl) pyrroles as Potential Antipsychotic Agents. Synthesis and Dopamine Receptor Binding", J. Med. Chem., 1995, pp. 4950-4952, vol. 38 No. 25.
Thurkauf, A., et al., 2-Pheynl-4-(aminomethyl) imidazoles as Potential Antipsychotic Agents. Synthesis and Dopamine D2 Receptor Binding:; J. Med. Chem.., 1995, pp. 2251-2255, vol. 38, No. 12, XP002203778.
Thurkauf, A. et al., "3-Aminomethylbiphenyls. A New Class of Dopamine Receptor Ligands", Med. Chem Res., 1996, pp. 69-80, vol. 6.
Whitney et al., J. Org. Chem. 1997, 62, 1264.
Wolfe, et al., Tetrahedron, 1996, 52(21), 7525.
Wolfe, J. et al., "Palladium-Catalyzed Amination of Aryl Triflates", J. Org. Chem. 1997, pp. 1264-1267, vol. 62, No. 5.
Yeager, et al., Synthesis, 1995, p. 28.
Avis, Kenneth E., Table of Contents, Pharmaceutical Dosage Forms, "Parenteral Medications", vols. 1 and 2.
Greene, Theodora W. et al., "Protective Groups in Organic Synthesis", Table of Contents, John Wiley & Sons, 1991.
Haines, Duane E., "Federation of European Neuroscience Societies 2000 Meeting", News from The American Association of Anatomists, the Anatomical Record, pp. 261, vol. 48.
Kinouchi, Keiko et al., "Evidence for $k_1$ opioid receptor multiplicity in the guinea pig cerebellum" European Journal of Pharmacology—Molecular Pharmacology Section, (1991), pp. 135-141, vol. 207.
Lieberman, Herbert A. , Table of Contents, "Pharmaceutical Dosage Forms Disperse Systems" vols. 1-3.
Lieberman, Herbert A., Table of Contents, Pharmaceutical Dosage Forms Tablets:, vols. 1-3.
McOmie, J.F.W. et al., "Protective Groups in Organic Synthesis", Table of Contents, Plenum Press 1973.
Rowe, Raymond C. et al., Table of Contents, "Handbook of Pharmaceutical Excipients", Fifth Edition.
Lambert, "The nociception/orphanin FQ receptor: a target with broad therapeutic potential" Nature Reviews, Aug. 2008, pp. 694-710, vol. 7.
Rover, et al., "ORL1 Receptor Ligands: Structure-Activity Relationships of 8-Cycloalkyl-1-Phenyl-1,3,8-Triaza-Spiro[4.5]decan-4-ones", Biorganic & Medicinal Chemistry Letters, 2000, pp. 831-834, vol. 10.
Jordan, et al., "8-(Heteroaryl)Phenalkyl-1-Phenyl-1,3,8-Triazaspiro[4.5]Decan-4-ones Opioid as Receptor Modulators" Medicinal Chemistry, 2005, pp. 601-610, vol. 1.
Wang, et al, " cDNA Cloning of an Orphan Opiate Receptor Gene Family Member and Its Splice Variant", FEBS Letters, 1994, pp. 75-79, vol. 348.
Chen, et al., "Molecular Cloning, Tissue Distribution and Chromosomal Localization of a Novel Member of the Opiod Receptor Gene Family", FEBS Letters, 1994, pp. 279-283, vol. 347.

(56) References Cited

OTHER PUBLICATIONS

Fukuda, et al., "cDNA Cloning and Regional Distribution of a Novel Member of the Opioid Receptor Family", FEBS Letters, 1994, pp. 42-46, vol. 343.
Bunzow, et al., "Molecular Cloning and Tissue Distribution of a Putative Member of the rat Opioid Receptor Gene family That is Not a μ, S or k Opioid Receptor Type", FEBS Letters, 1994, pp. 284288, vol. 347.
Ross, et al., "Aminopyrimidines as Neuroprotective Agents" American Chemical Society, Abstracts of Papers, 230$^{th}$ ACS National Meeting, Washington, DC United States, Aug. , Sep. 1, 2005, MEDI-039. AN 2005: 739554 Caplus.
Bröer, "Molecular Modelling Studies on the ORL1-Receptor and ORL1-Agonists", Journal of Computer-Aided Molecular Design, 2003, pp. 739-754, vol. 17.
Abdel-Magid, "Reductive Amination of Aldehydes and Ketones with Sodium Triacetoxyborohydride. Studies on Direct and Indirect Reductive Amination Procedures", J. Org. Chem., 1996, pp. 3849-3862, vol. 61.
Wichmann, "8-Acenaphthen-1-Yl-1-Phenyl-1,3,8-Triaza-Spiro[4.5]Decan-4-One Derivatives as Orphanin FQ Receptor Agonists", Bioorganic & Medicinal Chemistry Letters, 1999, pp. 2343-2348, vol. 9.
Wermuth, et al., The Latest Chemistry of Drug Discovery, last volume, Technomics, Inc. 1999. 9. 25 pp. 347 to 349, 359, 360, 452 and 453.
Okano, General Theory of New Pharmacology (Revised Third edition), Nankodo Co., Led., 1987. 4. 10 pp. 26, 111, 256 and 257.
US Office Action U.S. Appl. No. 12/479,103, Filing Date Aug. 30, 2011, OA Date Aug. 30, 2011.
US Office Action U.S. Appl. No. 11/939,789, Filing Date Nov. 14, 2007, OA Date Jan. 10, 2012.
US Office Action U.S. Appl. No. 11/939/789, Filing Date Nov. 14, 2007, OA Date Mar. 25, 2011.
(US Office Action) U.S. Appl. No. 11/939,789, Filing Date Nov. 14, 2007, OA Date Mar. 1, 2013.
(US Office Action U.S. Appl. No. 11/939,789, Filing Date Nov. 14, 2007, OA Date Apr. 16, 2012.
EP Search Report, 08729 809.7-2101, Date Dec. 22, 2011.
PCT International Search Report, PCT/US2009/056796, dated May 4, 2010.
PCT International Search Report, PCT/US2008/080081, dated Jul. 17, 2008.
PCT International Search Report, PCT/US2007/084751, dated Aug. 25, 2008.
PCT International Search Report, PCT/US2007/084642, dated Mar. 26, 2008.
U.S. Appl. No. 10/656,934, Office Action dated, Jul. 19, 2004.
U.S. Appl. No. 10/656,934, Office Action, dated Jul. 28, 2005.
U.S. Appl. No. 11/242,654, Office Action dated, May 29, 2008.
U.S. Appl. No. 11/242,654, Interview Summary dated, Jan. 3, 2009.
U.S. Appl. No. 11/398,239, Office Action dated, Mar. 20, 2009.
U.S. Appl. No. 10/909,858, Office Action dated Feb. 3, 2005.
U.S. Appl. No. 10/909,858, Office Action dated May 6, 2005.
U.S. Appl. No. 10/909,858, Office Action dated Jun. 14,2005 Examiner Interview.
U.S. Appl. No. 11/939,789 Office Action dated May 29, 2012.
U.S. Appl. No. 11/940,397, Office Action Dated Oct. 4, 2011.
U.S. Appl. No. 11/398,239, Notice of Allowance and Notice of Allowability dated Jul. 20, 2012.
U.S. Appl. No. 11/398,239, Notice of Allowance and Notice of Allowability dated Mar. 1, 2011.
PCT/US02/10736 ISR, dated Jun. 27, 2002.
EP ISR Application No. 02 721 678.7-2117, dated Mar. 4, 2004.
U.S. Appl. No. 10/656,934, Office Action dated, Mar. 2, 2006.
U.S. Appl. No. 10/656,934, NOA, and Notice of Allowability Sep. 8, 2005.
U.S. Appl. No. 10/656,934, Office Action dated, Jan. 27, 2006.
U.S. Appl. No. 11/242,654, NOA dated, Jan. 16, 2009.
U.S. Appl. No. 11/242,654, NOA dated, May 11, 2009.
U.S. Appl. No. 11/242,654, Interview Summary, dated May 15, 2008.
U.S. Appl. No. 12//327,437, Office Action dated, May 28, 2009.
U.S. Appl. No. 12/327,437, Office Action dated, Aug. 26, 2009.
U.S. Appl. No. 12/327,437, filed Dec. 3, 2008.
U.S. Appl. No. 12/327,437, NOA and Notice of Allowability, dated, Jan. 5, 2010.
U.S. Appl. No. 12/327,437, NOA, and Notice of Allowability, dated May 6, 2010.
U.S. Appl. No. 11/398,239, NOA dated Sep. 28, 2010.
U.S. Appl. No. 11/398,239, filed Apr. 5, 2006.
U.S. Appl. No. 11/939,789, filed Nov. 14, 2007.
U.S. Appl. No. 11/939,789, Office Action dated Aug. 23, 2010.
U.S. Appl. No. 11/939,789, Office Action dated Oct. 21, 2010.
U.S. Appl. No. 11/940,397, filed Nov. 15, 2007.
U.S. Appl. No. 11/940,397, Office Action dated Oct. 29, 2010.
U.S. Appl. No. 11/940,397, Office Action dated Apr. 15, 2010.
U.S. Appl. No. 12/479,103, Office Action dated Nov. 14, 2007.
U.S. Appl. No. 11/939,789, Office Action dated Mar. 1, 2013.
U.S. Appl. No. 11/939,789, Office Action dated Apr. 16, 2012.
U.S. Appl. No. 12/039,911, Office Action dated Feb. 28, 2008.
U.S. Appl. No. 12/039,911, Office Action dated Jul. 20, 2011.
U.S. Appl. No. 12/039,911, Office Action dated Jun. 14, 2012.
U.S. Appl. No. 12/030,911, Office Action dated Jun. 15, 2011.
U.S. Appl. No. 12/030,911, Office Action dated Feb. 2, 2012.
U.S. Appl. No. 12/030,911, Office Action dated Aug. 24, 2012.
U.S. Appl. No. 12/030,911, Office Action dated Dec. 12, 2012.
U.S. Appl. No. 12/030,911, NOA dated Apr. 23, 2013.
U.S. Appl. No. 12/030,911, Office Action dated Apr. 23, 2013.
U.S. Appl. No. 12/030,911, Office Action dated Jan. 10, 2013.
U.S. Appl. No. 10/656,934, Office Action dated May 11, 2005.
U.S. Appl. No. 10/656,934, Office Action dated Jul. 28, 2005.
U.S. Appl. No. 10/656,934, Office Action dated Feb. 16, 2006.
U.S. Appl. No. 10/656,934, Office Action dated Sep. 5, 2003.
U.S. Appl. No. 10/656,934, Office Action dated Jan. 28, 2005.
U.S. Appl. No. 12/327,437, Office Action dated Sep. 7, 2010.
EP Search Report, Application No. 03 749 479.7-1521, dated Sep. 9, 2008.
U.S. Appl. No. 12/327,437, Office Action dated, May 28, 2009.
U.S. Appl. No. 12/327,437, NOA and Notice of Allowability, May 6, 2010.
U.S. Appl. No. 12/327,437, NOA and Notice of Allowability, Apr. 3, 2013.
U.S. Appl. No. 12/327,437, NOA and Notice of Allowability, May 14, 2012.
U.S. Appl. No. 12/327,437, NOA and Notice of Allowability ,Jan. 5, 2010.
U.S. Appl. No. 10/909,858, Office Action dated Jun. 1, 2005.
U.S. Appl. No. 11/398,239, Office Action dated May 6, 2010.
PCT International Search Report, PCT/US03/27956, dated Feb. 18, 2004.
U.S. Appl. No. 12/327,437 NOA, and Notice of Allowability, Jan. 10, 2012.
U.S. Appl. No. 12/327,437 NOA, and Notice of Allowability, Jan. 7, 2011.
U.S. Appl. No. 12/327,437 NOA, and Notice of Allowability, Sep. 7, 2010.
Chung, et al., "Therapy for Cough: Active Agents", Pulmonary Pharmacology & Therapeutics, 2002, pp. 335-338, vol. 15.
Groneberg, et al., "Endogenous Opioids as Mediators of Asthma", Pulmonary Pharmacology & Therapeutics, 2001, pp. 383-389, vol. 14.
Wermuth, "Molecular Variations Based on Isosteric Replacements", The Practice of Medicinal Chemistry, 1996, pp. 203-237.
Wermuth, et al, The Latest Chemistry of Drug Discovery, last volume, Technomics, Inc. 1999, 9. 25 pp. 347 to 349, 359, 360, 452 and 453.
Okano, General Theory of New Pharmacology (Revised Third edition), Nankodo Co., Led., 1987, 4, 10 pp. 26, 111, 256 and 257.
Meuiner, J. et al., "Isolation and Structure of the Endogenous Agonist of Opioid Receptor-Like ORL$_1$ Receptor", Nature, Oct. 12, 1995, pp. 532-535, vol. 377.

(56) References Cited

OTHER PUBLICATIONS

Ciccocioppo, et al., "Effect of nociceptin on alcohol intake in alcohol-preferring rats", Psychopharmacology, 1999, pp. 220-224, vol. 141.

Ciccocioppo, et al., "The nociceptin/orphanin FQ/NOP receptor system as a target for treatment of alcohol abuse: a review of recent work in alcohol-preferring rats", Physiology & Behavior, 2003, pp. 121-128, vol. 79.

Polidori, et al., "Pharmacological characterization of the nociceptin receptor mediating hyperphagia: identification of a selective antagonist", Psychopharmacology, 2000, pp. 430-437, vol. 148.

Peiser, et al., "Nociceptin Effects in the Airways", Peptides, 2000, pp. 995-998, vol. 21.

Redrobe, et al., Nociceptin receptor Antagonists display antidepressant-like Properties in the Mouse forced Swimming Test:, Naunyn-Schmiedeberg's Arch Pharmacol, 2002, pp. 164-167, vol. 365.

Wise, et al., "Examination of a Series of 8-[3-[Bis(4-fluorophenyl)amino]propyl]-1-aryl-1,3,8-triazaspiro[4.5]decan-4-ones as Potential Antipsychotic Agents", J. Med. Chem. 1985, pp. 1811-1817, vol. 28.

Rizzi, et al., "Nociceptin Receptor Activation Inhibits Tachykinergic Non Adrenergic Non Cholinergic Contraction of Guinea Pig Isolated Bronchus", Pharmacology Letters, 1999; vol. 64, No. 13, pp. 157-163.

Reply dated Jul. 3, 2012 to Examining Division's communication dated Feb. 22, 2012 in EP 07845080.6.

* cited by examiner

SALTS OF 3-(3-AMINO-2-(R)-HYDROXY-PROPYL)-1-(4-FLUORO-PHENYL)-8-(8-METHYL-NAPHTHALEN-1-YLMETHYL)-1,3,8-TRIAZA-SPIRO[4.5]DECAN-4-ONE

CROSS REFERENCE TO RELATED APPLICATIONS

This application claims the benefit of U.S. Provisional Application 60/861,378, filed on Nov. 28, 2006, which is incorporated by reference herein in its entirety.

FIELD OF THE INVENTION

The present invention is directed to salts of 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one, pharmaceutical compositions containing them and their use in the treatment of disorders and conditions modulated by NOP. The present invention is further directed to process(es) for the preparation of 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one and the salts of 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one.

BACKGROUND OF THE INVENTION

The ORL-1 (orphan opioid receptor) G-protein coupled receptor, also known as the nociceptin receptor, was first reported in 1994, and was discovered based on its homology with the classic delta-(OP-1), mu-(OP-3), and kappa-(OP-2) opioid receptors. The ORL-1 G-protein coupled receptor does not bind opioid ligands with high affinity. The amino acid sequence of ORL-1 is 47% identical to the opioid receptors overall, and 64% identical in the transmembrane domains. (*Nature*, 1995, 377, 532.)

The endogenous ligand of ORL-1, known as nociceptin or nociceptin/orphanin FQ Peptide or NOP, a highly basic 17 amino acid peptide, was isolated from tissue extracts in 1995. It was named both nociceptin, because it increased sensitivity to pain when injected into mouse brain, and orphanin FQ (OFQ) because of the terminal phenylalanine (F) and glutamine (Q) residues that flank the peptide on the N- and C-termini respectively. (WO97/07212)

NOP binding to ORL-1 receptors causes inhibition of cAMP synthesis, inhibition of voltage-gated calcium channels, and activation of potassium conductance. In vivo, nociceptin produces a variety of pharmacological effects that at times oppose those of the opioids, including hyperalgesia and inhibition of morphine-induced analgesia. Mutant mice lacking nociceptin receptors show better performance in learning and memory tasks. These mutant mice also have normal responses to painful stimuli.

The ORL-1 receptor is widely distributed/expressed throughout the human body, including in the brain and spinal cord. In the spinal cord, the ORL-1 receptor exists in both the dorsal and ventral horns, and precursor mRNA has been found in the superficial lamina of the dorsal horn, where primary afferent fibers of nociceptors terminate. Therefore, the ORL-1 has an important role in nociception transmission in the spinal cord. This was confirmed in recent studies wherein nociceptin, when given to mice by i.c.v. injection, induced hyperalgesia and decreased locomotor activity. (*Brit. J. Pharmacol.* 2000, 129, 1261.)

Battista et al., in US Publication 2004/0142955, published Jul. 22, 2004 disclose hydroxy alkyl substituted 1,3,8-triaza-spiro[4.5]decan-4-one derivatives useful in the treatment of disorders and conditions mediated by the ORL-1 G-protein coupled receptor, and more particularly the compound of formula (Is)

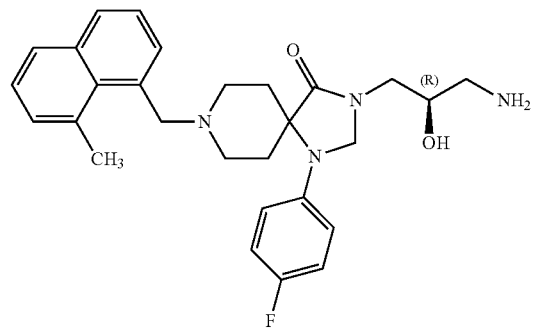

and pharmaceutically acceptable salts thereof. The compound of formula (Is) is also known as 3-(3-amino-2(R)-hydroxy-propyl)-1-(4-fluoro-phenyl)-8-(8-methyl-naphthalen-1-ylmethyl)-1,3,8-triaza-spiro[4.5]decan-4-one.

SUMMARY OF THE INVENTION

The present invention is directed to acid addition salts of the compound of formula (Is)

(Is)

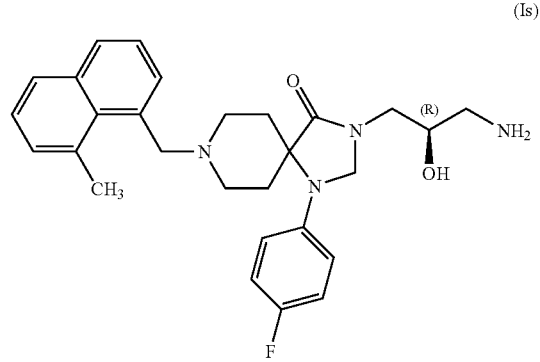 [SMILES: Cc1cccc2cccc(CN3CCC4(CC3)C(=O)N(C[C@H](O)CN)CN4c3ccc(F)cc3)c12]

wherein the salt is formed at the terminal amine of the compound of formula (Is) and wherein the acid anion is selected from the group consisting of sulfate, fumarate, hydrochloride and 2-keto-L-gulonic acid salts.

In an embodiment of the present invention, the salt of the compound of formula (Is) is selected from the group consisting of mono-sulfate, mono-fumarate, mono-hydrochloride, di-hydrochloride and bis-(2-keto-L-gulonic acid) salts. In another embodiment of the present invention, the salt of the compound of formula (Is) is mono-sulfate salt of the compound of formula (Is). In another embodiment of the present invention, the salt of the compound of formula (Is) is a pharmaceutically acceptable salt.

The present invention is further directed to a process for the preparation of the compound of formula (Is)

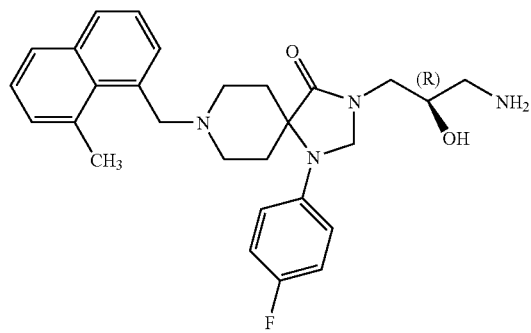

comprising

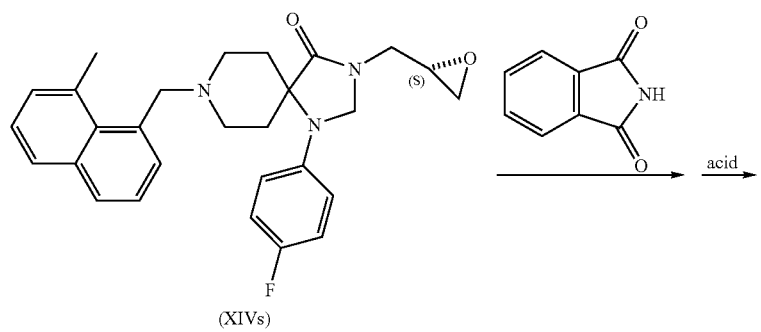

reacting with isoindole-1,3-dione; and then reacting with an acid, in the presence of an inorganic base; to yield the corresponding compound of formula (Is).

The present invention is further directed to a process for the preparation of an acid addition salt of the compound of formula (Is)

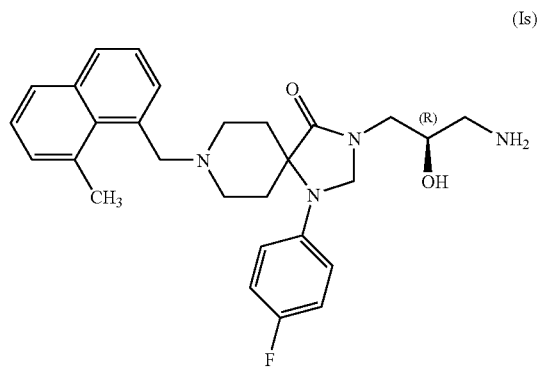 [SMILES: Cc1cccc2cccc(CN3CCC4(CC3)C(=O)N(C[C@H](O)CN)CN4c3ccc(F)cc3)c12]

comprising reacting the compound of formula (Is) with an acid, to yield the corresponding acid addition salt.

In an embodiment of the present invention, the acid is selected from the group consisting of sulfuric acid, fumaric acid, hydrochloric acid and 2-keto-L-gulonic acid. In another embodiment of the present invention, the acid is sulfuric acid.

The present invention is further directed to a process for the preparation of a crystalline, mono-sulfate salt of the compound of formula (Is)

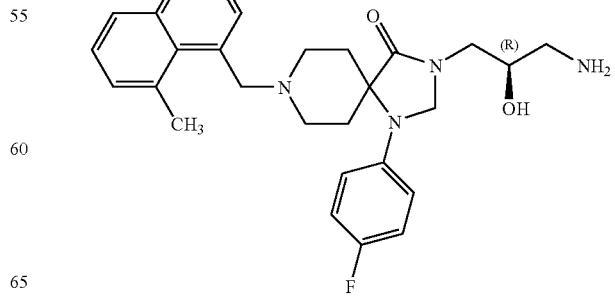

comprising (a) reacting a compound of formula (Is) with 2-keto-L-gulonic acid; to yield the corresponding bis-2-keto-L-gulonic acid salt of the compound of formula (Is); and (b) reacting the bis-2-keto-L-gulonic acid salt of the compound of formula (Is) with sulfuric acid, in the presence of water, in an alcohol;

to yield the corresponding crystalline, mono-sulfate salt of the compound of formula (Is).

The present invention is further directed to a process for the purification of a crystalline, mono-sulfate salt of the compound of formula (Is)

(Is)

comprising re-crystallizing the mono-sulfate salt of the compound of formula (Is) from an alcohol/water mixture.

The present invention is further directed to a product prepared according to the process described herein.

Illustrative of the invention is a pharmaceutical composition comprising a pharmaceutically acceptable carrier and any of the salts of the compound of formula (I) as described herein. An illustration of the invention is a pharmaceutical composition made by mixing any of the salts of the compound of formula (I) as described herein and a pharmaceutically acceptable carrier. Illustrating the invention is a process for making a pharmaceutical composition comprising mixing any of the salts of the compound of formula (I) as described herein and a pharmaceutically acceptable carrier.

Exemplifying the invention are methods of treating a disorder or condition mediated by the ORL-1 receptor, (selected from the group consisting anxiety, depression, panic, mania, dementia, bipolar disorder, substance abuse (for example, alcohol abuse), neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, impaired cognition, impaired memory and for mood stabilization) comprising administering to a subject in need thereof a therapeutically effective amount of any of the salts or pharmaceutical compositions described above.

Another example of the invention is the use of any of the salts described herein in the preparation of a medicament for treating: (a) anxiety, (b) depression, (c) panic, (d) mania, (e) dementia, (f) bipolar disorder, (g) substance abuse (h) neuropathic pain, (i) acute pain, (j) chronic pain, (k) migraine, (l) asthma, (m) cough, (n) psychosis, (o) schizophrenia, (p) epilepsy, (q) hypertension, (r) obesity, (s) eating disorders, (t) cravings, (u) diabetes), (v) cardiac arrhythmia, (w) irritable bowel syndrome, (x) Crohn's disease, (uy) urinary incontinence, (z) adrenal disorders, (aa) attention deficit disorder (ADD), (bb) attention deficit hyperactivity disorder (ADHD), (cc) Alzheimer's disease, for (dd) improved cognition, (ee) improved memory and (ff) mood stabilization, in a subject in need thereof.

DETAILED DESCRIPTION OF THE INVENTION

The present invention is directed to acid addition salts of the compound of formula (Is)

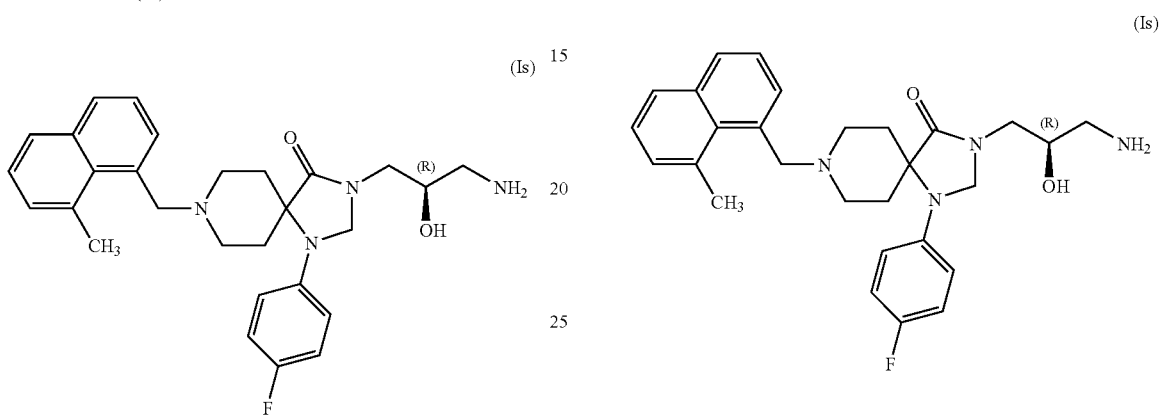

(Is)

wherein the salt is formed at the terminal amine of the compound of formula (Is) and wherein the acid anion is selected from the group consisting of sulfate, fumerate, hydrochloride and 2-keto-L-gulonic acid salts. In an embodiment of the present invention, the salt of the compound of formula (Is) is selected from the group consisting of mono-sulfate, mono-fumerate, mono-hydrochloride, di-hydrochloride and di-(2-keto-L-gulonic acid) salts. In another embodiment of the present invention, the salt of the compound of formula (Is) is a mono-sulfate of the compound of formula (Is).

In an embodiment of the present invention, the acid addition salt of the compound of formula (Is), preferably, the crystalline, mono-sulfate salt of the compound of formula (Is) is substantially pure.

In an embodiment, the present invention is directed to a sulfate salt of the compound of formula (Is). In another embodiment of the present invention, the sulfate salt of the compound of formula (Is) is crystalline. In another embodiment of the present invention, the sulfate salt of the compound of formula (Is) is non-hygroscopic. In another embodiment of the present invention, the sulfate salt of the compound of formula (Is) is a mono-sulfate salt. In another embodiment of the present invention, the sulfate salt is anhydrous. Preferably, the sulfate salt of the compound of formula (Is) is a crystalline, non-hygroscopic, anhydrous, mono-sulfate salt of the compound of formula (Is).

In an embodiment, the present invention is directed to a 2-keto-L-gulonic acid salt of the compound of formula (Is). In another embodiment of the present invention, the 2-keto-L-gulonic acid salt of the compound of formula (Is) is crystalline. In another embodiment of the present invention, the 2-keto-L-gulonic acid salt of the compound of formula (Is) is non-hygroscopic. In another embodiment of the present invention, the 2-keto-L-gulonic acid salt of the compound of formula (Is) is a bis-2-keto-L-gulonic acid salt. Preferably, the 2-keto-L-gulonic acid salt of the compound of formula (Is) is a crystalline, non-hygroscopic, bis-2-keto-L-gulonic acid salt.

In an embodiment, the present invention is directed to a fumerate salt of the compound of formula (Is). In another embodiment of the present invention, the fumerate salt of the compound of formula (Is) is amorphous.

In an embodiment, the present invention is directed to a hydrochloride salt of the compound of formula (Is). In another embodiment of the present invention, the hydrochloride salt of the compound of formula (Is) is mono-hydrochloride or di-hydrochloride salt of the compound of formula (Is). In another embodiment of the present invention, the mono-hydrochloride and di-hydrochloride salts of the compound of formula (Is) are crystalline. DVS measurements completed on the mono-hydrochloride and di-hydrochloride salts of the compound of formula (Is) indicate that both of these salt forms are hygroscopic.

Abbreviations used in the specification, particularly the Schemes and Examples, are as follows:

| | |
|---|---|
| DMAC = | N,N-Dimethylacetamide |
| DMF = | N,N-Dimethylformamide |
| DMSO = | Dimethylsulfoxide |
| DVS = | Differential Vapor Sorption |
| IPA = | Isopropyl Alcohol |
| LiHMDS = | Lithium bis(trimethylsilyl)amide |
| MTBE = | Methyl t-butyl ether |
| NaBH(OAc)$_3$ = | Sodium triacetoxyborohydride |
| THF = | Tetrahydrofuran |

As used herein, unless otherwise noted, the term "substantially pure salt" shall mean that the mole percent of impurities in the isolated salt is less than about 5 mole percent, preferably less than about 2 mole percent, more preferably, less than about 0.5 mole percent, most preferably, less than about 0.1 mole percent.

As used herein, unless otherwise noted, the term "disorder or condition mediated by the ORL-1 receptor" shall include any disorder, disease, syndrome or condition wherein at least one of the symptoms and/or manifestations of the disorder, disease, syndrome or condition is, at least in part, mediated through the ORL-1 receptor.

Suitable examples include, but are not limited to anxiety, depression, panic, mania, dementia, bipolar disorder, substance abuse (for example, alcohol abuse), neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, impaired cognition, impaired memory and for mood instability (wherein the salts of the present invention are used for mod stabilization). Preferably, the disorder or condition mediated by the ORL-1 receptor is selected from the group consisting of depression, anxiety, substance abuse (more preferably, alcohol abuse, addiction or dependency) and eating disorders.

As used herein, unless otherwise noted, the term "eating disorders" shall mean any disorder associated with eating. Suitable examples include, but are not limited to anorexia nervosa, bulimia, binge eating, food cravings, and the like.

As used herein, unless otherwise noted, the term "adrenal disorders" shall mean disorders mediated by the adrenal gland. Suitable examples include, but are not limited to Cushing's syndrome, Addison's disease, and the like.

As used herein, unless otherwise noted, the term "substance abuse" shall include substance abuse, addiction and/or dependency, wherein the substance of abuse is any legal or illegal substance which a subject or patient may abuse and/or to which a subject or patient may develop an addiction or dependency. Suitable examples include, but are not limited to alcohol, cocaine, heroine, methamphetamine, ketamine, 3,4 methylenedioxymethylamphetamine (also known as Ecstasy), nicotine, oxycontin/oxycodone, codeine, morphine, and the like. Preferably, the substance of abuse is selected from the group consisting of alcohol, cocaine, heroine and nicotine. More preferably, the substance of abuse is alcohol.

As used herein, the term "composition" is intended to encompass a product comprising the specified ingredients in the specified amounts, as well as any product which results, directly or indirectly, from combinations of the specified ingredients in the specified amounts.

As used herein, the term "therapeutically effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "subject" refers to an animal, preferably a mammal, most preferably a human, who has been the object of treatment, observation or experiment. Preferably, the subject has experienced and/or exhibited at least one symptom of the disease or disorder to be treated and/or prevented.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention is directed to a process for the preparation of the compound of formula (Is), also known as 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one. The present invention is further directed to a process for the preparation of a 2-keto-L-gulonic acid salt of the compound of formula (Is). The present invention is further directed to a process for the preparation of a sulfate salt of the compound of formula (Is).

More specifically, the present invention is directed to a processes for the preparation of the compound of formula (Is), a bis-2-keto-L-gulonic acid salt of the compound of formula (Is) and a mono-sulfate salt of the compound of formula (Is), wherein said processes are suitable for large scale manufacture of the compound of formula (Is), as outlined in more detail Scheme 1, below.

Scheme 1

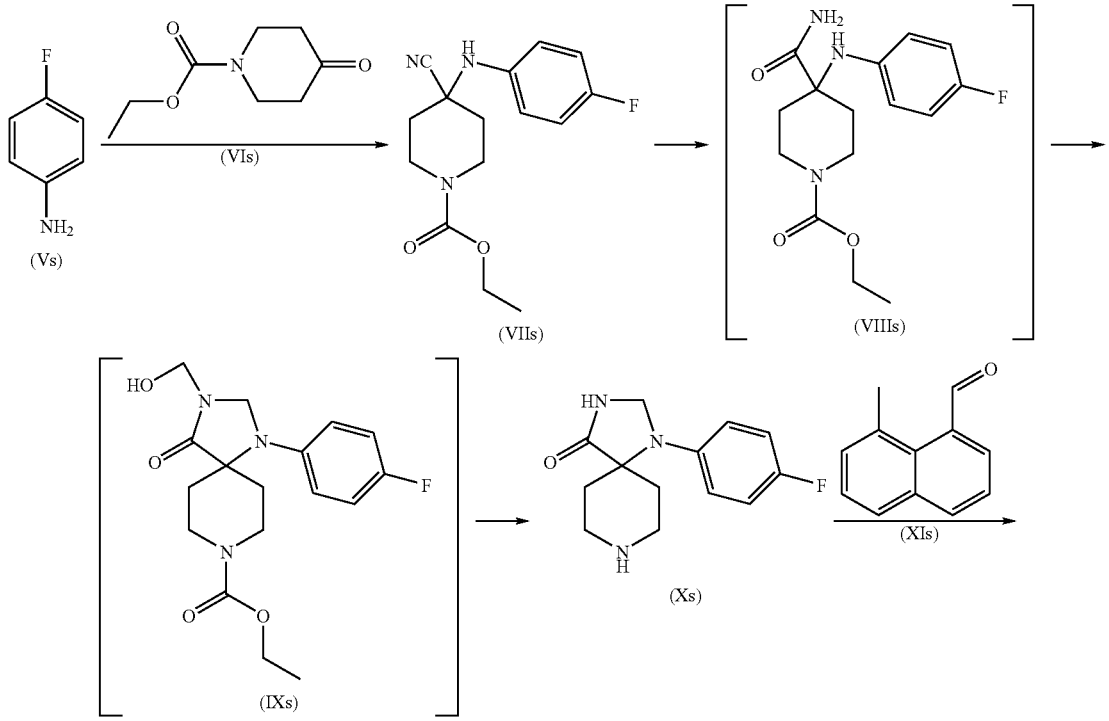

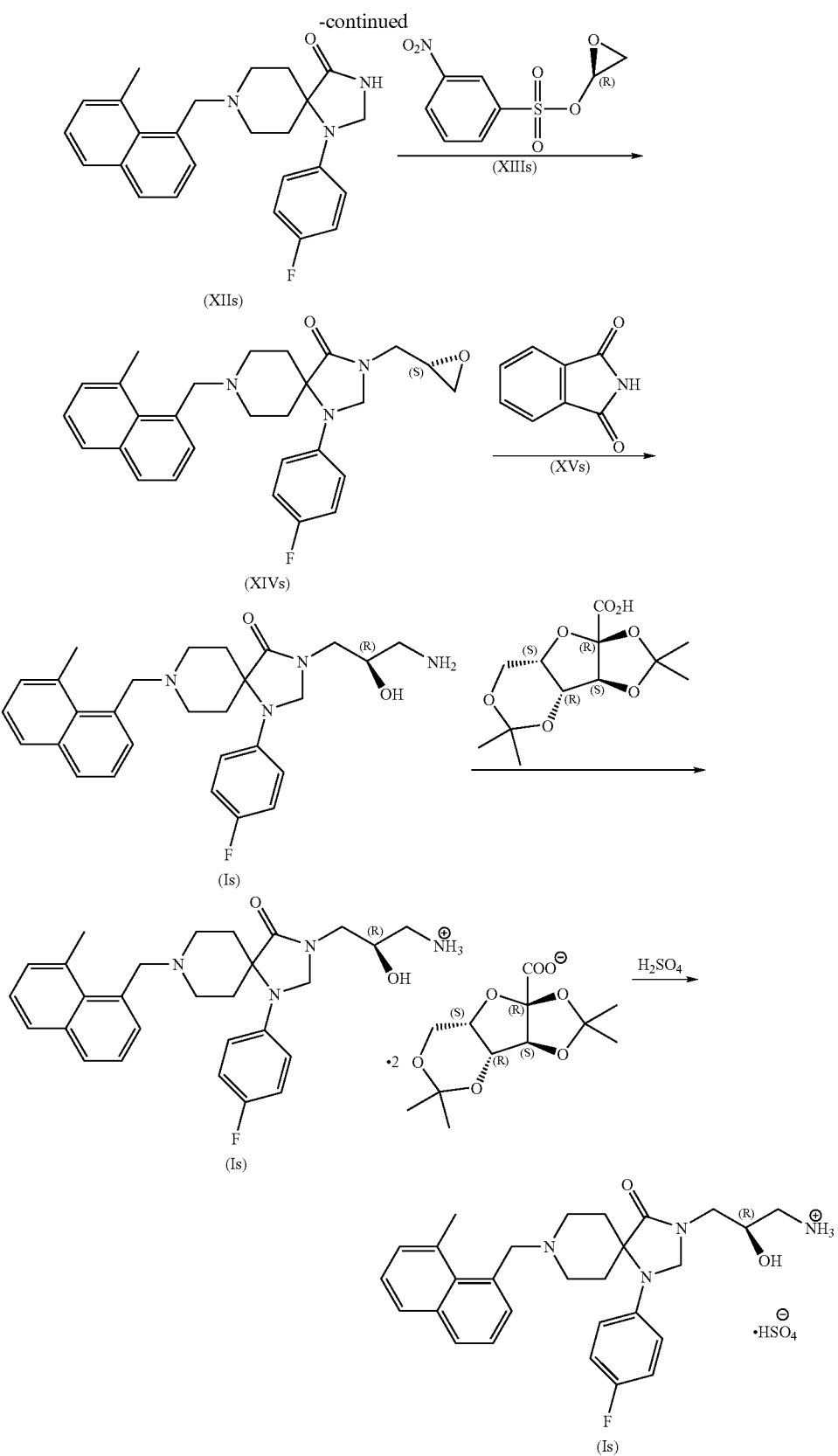
Accordingly, a suitably substituted compound of formula (Vs), also known as 4-fluoro-phenylamine, a known compound or compound prepared by known methods, is reacted with a compound of formula (VIs), also known as 4-oxopiperidine-1-carboxylic acid ethyl ester, a known compound or compound prepared by known methods; in the presence of HCN or a salt thereof, such as aqueous sodium cyanide, potassium cyanide, and the like; in the presence of a carboxylic acid such as acetic acid, propionic acid, oxaylic acid, and the like; in an organic solvent such as IPA, acetonitrile, and the like, to yield the corresponding compound of formula (VIIs).

The compound of formula (VIIs) is reacted with an oxidizing agent such as hydrogen peroxide, and the like; in the presence of a base such as potassium carbonate, and the like; in an organic solvent or a mixture of an organic solvent and water such as a mixture of water and DMSO; to yield the corresponding compound of formula (VIIIs), which compound is preferably not isolated.

The compound of formula (VIIIs) is reacted with an acid (preferably a weak acid) such as acetic acid, propionic acid, and the like, in an organic solvent such as DMSO, IPA, and the like, preferably in the same solvent as the previous reaction step, to yield the corresponding compound of formula (IXs).

The compound of formula (IXs) is reacted with an inorganic base (preferably a strong inorganic base) such as potassium hydroxide, sodium hydroxide, choline, and the like, in water; to yield the corresponding compound of formula (Xs).

The compound of formula (Xs) is reacted with a compound of formula (XIs), also known as 8-methyl-naphthalene-1-carbaldehyde, a known compound or compound prepared by known methods, in the presence of a reducing agent/hydride source and such as $NaBH(OAc)_3$, $NaCNBH_4$, and the like; in an organic solvent or a mixture of water and an organic solvent such as a mixture of THF and water, IPA, DMF, and the like, to yield the corresponding compound of formula (XIIs).

The compound of formula (XIIs) is reacted with a compound of formula (XIIIs), also known as 3-nitro-benzenesulfonic acid oxiranyl ester, a known compound or compound prepared by known methods; in the presence of a base (preferably a strong base) such as potassium t-butoxide, NaH, LiHMDS, and the like; in an organic solvent or mixture of organic solvents such as a mixture of THF and ethyl acetate, MTBE, and the like, to yield the corresponding compound of formula (XIVs).

The compound of formula (XIVs) is reacted with a compound of formula (XVs), also known as isoindole-1,3-dione, a known compound or compound prepared by known methods, in an organic solvent such as DMF, DMSO, DMAC, and the like; and then reacted with an acid such as sulfuric acid, and the like, in water; in the presence of an inorganic base such as calcium hydroxide, and the like; to yield the corresponding compound of formula (Is).

Preferably, the compound of formula (Is) is isolated and/or purified according to known methods. The compound of formula (Is) may be isolated for example, by filtration, by evaporation of solvent or other suitable method. The compound of formula (Is) may be purified for example, by recrystallization, by column chromatography or other suitable method.

For example, the compound of formula (Is) may be isolated as follows: the calcium salt of the compound of formula (Is), prepared as described above may be isolated by filtration, then acidified by treating with a suitably selected acid, to yield the compound of formula (Is), which is further isolated by extraction, then crystallized according to known methods.

Preferably, the compound of formula (Is) is isolated by crystallization. Preferably, the compound of formula (Is) is purified by recrystallization for a suitable organic solvent such as MTBE/water, IPA/water, and the like, more preferably from a mixture of MTBE/water.

The compound of formula (Is) is then optionally reacted with 2-keto-L-gulonic acid, a known compound or compound prepared by known methods, in an organic solvent such as IPA, and the like, to yield the corresponding bis-2-keto-L-gulonic acid salt of the compound of formula (Is).

Preferably, the bis-2-keto-L-gulonic acid salt of the compound of formula (Is) is isolated by crystallization from IPA. Preferably, the bis-2-keto-L-gulonic acid salt of the compound of formula (Is) is purified by recrystallization for a suitable organic solvent such as IPA, and the like, more preferably from IPA.

The bis-2-keto-L-gulonic acid salt of the compound of formula (Is), is then optionally converted to the corresponding mono-sulfate salt of the compound of formula (Is), by reacting with sulfuric acid, in the presence of water, in an alcohol, such as ethanol, methanol, IPA, and the like.

The mono-sulfate salt of the compound of formula (Is) is preferably isolated according to known methods, for example by filtration. The mono-sulfate salt of the compound of formula (Is) is further preferably purified according to known methods, for example by recrystallization from a suitably selected solvent or mixture of solvents such as ethanol and water, IPA/water, and the like, more preferably from a mixture of ethanol and water.

Alternatively, the mono-sulfate salt of the compound of formula (Is) may be prepared by reacting the compound of formula (Is) with sulfuric acid, in an organic solvent such as an alcohol, such as ethanol, and the like, to yield the corresponding mono-sulfate salt of the compound of formula (Is). The mono-sulfate salt of the compound of formula (Is) is preferably isolated according to known methods, for example by filtration and further, optionally purified according to known methods, for example by recrystallization.

The fumerate salt of the compound of formula (Is) may be prepared by reacting the compound of formula (Is) with fumaric acid in an organic solvent such as methanol, and the like. The mono-hydrochloride salt of the compound of formula (Is) may be prepared by reacting the compound of formula (Is) with aqueous hydrochloric acid in an organic solvent such as methanol, 3-methyl-1-butanol, and the like. The di-hydrochloride salt of the compound of formula (Is) may be prepared by reacting the compound of formula (Is) with aqueous hydrochloric acid in an organic solvent such as methanol, n-butanol, and the like.

The fumerate, mono-hydrochloride or di-hydrochloride salt of the compound of formula (Is) may be further optionally purified according to known methods, for example by recrystallization, and the like.

The crystalline bis-2-keto-L-gulonic acid and crystalline mono-sulfate salts of the compound of formula (Is) may be characterized by their respective X-ray Powder Diffraction patterns. The X-ray Powder Diffraction patterns were measured utilizing a powder X-ray diffractometer, using $CuK_\alpha$ radiation and suitably selected system conditions, as listed below:

a) $CuK\alpha$ radiation, 30 mA, 40 KV b) $\frac{1}{12}°$ divergence slit, 0.2 receiving slit c) Scanning from 4 to 30° 2θ at a scan rate of 0.017° 2θ/second d) Aluminum sample holder The crystalline bis-2-keto-L-gulonic acid and crystalline mono-sulfate salts of the compound of formula (Is) may be characterized by their XRD spectra which may be identified by their 2θ, d-spacing and optionally their relative intensity values. In an embodiment, the crystalline bis-2-keto-L-gulonic acid and crystalline mono-sulfate salts of the compound of formula (Is) may be characterized by their respective XRD spectra comprising peaks with a relative intensity of greater than or equal to about 10%, preferably about 25%.

The crystalline bis-2-keto-L-gulonic acid salt of the compound of formula (Is) may be characterized by its XRD spectra which comprises the following peaks:

TABLE 1

Bis-2-keto-L-gulonic Acid Salt

| Pos. [°2Th.] | d-spacing [Å] | Relative Intensity [%] |
| --- | --- | --- |
| 4.36 | 20.25 | 36.42 |
| 5.91 | 14.94 | 10.84 |
| 6.44 | 13.72 | 33.47 |
| 6.73 | 13.14 | 43.69 |
| 7.09 | 12.47 | 89.40 |
| 8.76 | 10.09 | 13.78 |
| 9.44 | 9.36 | 20.47 |
| 12.30 | 7.20 | 76.82 |
| 12.93 | 6.84 | 30.28 |
| 14.01 | 6.32 | 14.72 |
| 15.34 | 5.78 | 81.23 |
| 15.48 | 5.72 | 78.77 |
| 16.28 | 5.44 | 21.28 |
| 16.69 | 5.31 | 100.00 |
| 17.09 | 5.19 | 56.31 |
| 17.84 | 4.97 | 98.92 |
| 18.49 | 4.80 | 32.55 |
| 18.94 | 4.68 | 30.60 |
| 19.76 | 4.49 | 20.53 |
| 20.09 | 4.42 | 21.15 |
| 20.67 | 4.30 | 22.76 |
| 23.53 | 3.78 | 9.91 |
| 24.11 | 3.69 | 28.47 |
| 24.45 | 3.64 | 19.10 |

The crystalline mono-sulfate salt of the compound of formula (Is) may be characterized by its XRD spectra which comprises the following peaks:

TABLE 2

Sulfate Salt

| Pos. [°2Th.] | d-spacing [Å] | Relative Intensity [%] |
| --- | --- | --- |
| 5.74 | 15.40 | 71.81 |
| 8.12 | 10.89 | 18.52 |
| 9.20 | 9.61 | 45.67 |
| 11.60 | 7.63 | 42.97 |
| 14.74 | 6.01 | 16.18 |
| 14.98 | 5.92 | 16.75 |
| 15.51 | 5.71 | 7.65 |
| 16.30 | 5.44 | 14.14 |
| 16.58 | 5.35 | 9.66 |
| 17.06 | 5.20 | 8.04 |
| 17.28 | 5.13 | 13.65 |
| 18.22 | 4.87 | 100.00 |
| 19.33 | 4.59 | 12.77 |
| 19.60 | 4.53 | 31.86 |
| 20.80 | 4.27 | 30.11 |
| 21.64 | 4.11 | 38.87 |
| 22.04 | 4.03 | 19.09 |

The present invention further comprises pharmaceutical compositions containing one or more of the salts of the compound of formula (Is) as described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-1000 mg, or any range therein and may be given at a dosage of from about 0.01-300 mg/kg/day, or any range therein, preferably from about 0.5-50 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, auto injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders and conditions mediated by the ORL-1 receptor described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 10 to 500 mg of the compound, or any range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, one or more of the salts of the compound of formula (Is) as described herein, as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications, Volumes 1-2*, edited by Avis et al; and *Pharmaceutical Dosage Forms: Disperse Systems*, Volumes 1-2, edited by Lieberman et al; published by Marcel Dekker, Inc.

The salts of the present invention may be administered in any of the foregoing compositions and according to dosage regimens established in the art whenever treatment of disorders or conditions mediated by the ORL-1 receptor is required.

The daily dosage of the products may be varied over a wide range from 0.01 mg/kg to 300 mg/kg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any range therein. Preferably, the range is from about 0.5 to about 100.0 mg/kg of body weight per day, or any range therein. More preferably, from about 1.0 to about 50.0 mg/kg of body weight per day, or any range therein. More preferably, from about 1.0 to about 25.0 mg/kg of body weight per day, or any range therein. More preferably, from about 1.0 to about 5.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Examples 1, 2 and 3 below are recipes/procedures for the synthesis and/or purification and/or crystallization of the titled compounds. Several batches of the titled compounds were prepared using the recipes as described below.

Example 1

Crystallization of Bis-2-Keto-L-Gulonic Acid Salt of the Compound of Formula (Is)

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one (30 g) was heated to dissolution in IPA (100 mL) and the resulting mixture, maintained at 70-80° C. was treated with a warm solution of 2-keto-L-gulonic acid (68.7 g, 0.235 mol) in IPA (250 g). The reaction mixture was maintained at this temperature for about 15-30 min and then cooled to 25° C. over about 1-2 h. The resulting solids were collected by vacuum filtration, washed with IPA (70 g), then dried in a vacuum oven at 60° C. to yield the title compound as a solid.

Example 2

Preparation of Mono-Sulfate Salt of Compound of Formula (Is) Directly from Bis-2-Keto-L Gulonic Acid Salt of Compound of Formula (Is)

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one, bis-2-keto-L-gulonic acid salt (10 g, 10 mmol) and sulfuric acid (1.1 g, 11 mmol) in water (11 mL) were heated to about 75-80° C., and then the resulting solution was treated with ethanol (60 g). Upon cooling to 50° C. a precipitate was formed. The reaction mixture was cooled to 20-25° C. over about 1.5 to 2 h and then stirred for about 10-12 h. The solids were filtered, washed with ethanol (30 g) and dried in a vacuum oven at 60° C. to yield the title compound as a solid.

Example 3

Recrystallization of Mono-Sulfate Salt of Compound of Formula (Is)

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one, bis-2-keto-L-gulonic acid salt (3.3 g, 5.74 mmol) in water (95 mL) was heated to 100° C. The resulting solution was hot filtered and the filtrate was concentrated under reduced pressure and temperature (50 mbar, 60° C.) to remove approximately 80 g of water. While maintaining the reaction temperature between 60-70° C., ethanol (34 mL) was added. After precipitation began the reaction was cooled to 25° C. over a period of about 1.5 to 2 h and stirring was continued for about 12-14 h. The solid was isolated by vacuum filtration and washed with water (2×7 mL) and ethanol (9 mL). The solids were dried in a vacuum oven at 60° C. to yield the title compound as a solid.

Example 4

Preparation of Crystalline, Mono-Sulfate Salt of Compound (Is)

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one (50 mg) in ethanol (1 mL) was treated with 1 eq of 18M $H_2SO_4$ and water (0.2 mL), then heated to dissolve the solids. The resulting solution was then allowed to cool slowly to room temperature overnight. The resulting solid was collected and dried on a filter pad to yield the title compound as a solid.

Initial onset of melt at 196° C., with peaks at 210° C. and 224° C.

Example 5

Preparation of Mono-Hydrochloride Salt of Compound (Is)

3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one (0.5 g, 1.0 mmole) in methanol (10 mL) and 3-methyl-1-butanol (5 mL) were treated with hydrogen chloride (in diethyl ether, 1.05 mmoles; 1.05 mL). The resulting mixture was warmed to 80° C. and then diluted with methanol (1 mL). Upon cooling a precipitate was observed. The solid was filtered, washed with IPA and dried to yield the title compound as a white solid.

Example 6

Preparation of Di-Hydrochloride Salt of Compound (Is)

The title compound was prepared in a well plate reacting 3-(3-Amino-2-(R)-hydroxy-propyl)-1-(4-fluoro-phenyl)-8-(8-methyl-naphthalen-1-ylmethyl)-1,3,8-triaza-spiro[4.5]decan-4-one with 1 equivalent HCl (aq) in a 1:1 mixture of methanol/1-butanol (450 mg/mL of each). The solvent was slowly evaporated to yield the title compound as a residue.

Example 7

Solid Dosage Forms Comprising Crystalline, Mono-Sulfate Salt of 3-(3-amino-2-(R)-hydroxy-propyl)-1-(4-fluoro-phenyl)-8-(8-methyl-naphthalen-1-ylmethyl)-1,3,8-triaza-spiro[4.5]decan-4-one Solid, tablet dosage forms comprising the crystalline, mono-sulfate salt of the compound of formula (Is) were prepared with compositions as listed in Table 3. The ingredients were mixed and compressed into tablets, according to known methods. In the table below, the abbreviation BHA stands for butylated hydroxytoluene and the abbreviation BTA stands for butylated hydroxyanisole. PROSOLV HD90® is solidified high density microcrystalline cellulose composed of 98% microcrystalline cellulose and 2% colloidal silicon dioxide. CROSPOVIDONE is a synthetic homopolymer of cross-linked N-vinyl-2-pyrrolidone.

TABLE 3

Solid Tablet Dosage Forms

| | | (mg) | (mg) | (mg) | (mg) | (mg) |
|---|---|---|---|---|---|---|
| Compound (Is) | Active | 1.0 | 5.0 | 25.0 | 100.0 | 250.0 |
| PROSOLV HD90 ® | Filler | 62.83 | 314.15 | 44.84 | 179.36 | 448.40 |
| CROSPOVIDONE | Disintegrant | 4.0 | 20.0 | 4.0 | 16.0 | 40.0 |
| BHT | Antioxidant | 0.035 | 0.175 | 0.035 | 0.14 | 0.35 |
| BHA | Antioxidant | 0.035 | 0.175 | 0.035 | 0.14 | 0.35 |
| Stearic Acid | Lubricant | 2.1 | 10.5 | 2.29 | 9.16 | 22.9 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A crystalline, mono-sulfate salt of a compound of formula (Is)

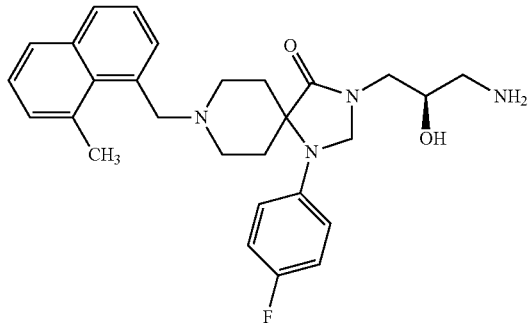

comprising the X-ray powder diffraction pattern peaks at °2 theta: 5.74, 8.12, 9.20, 11.60, 14.74, 14.98, 15.51, 16.30, 16.58, 17.06, 17.28, 18.22, 19.33, 19.60, 20.80, 21.64, and 22.04.

2. A pharmaceutical composition comprising a pharmaceutically acceptable carrier and the salt of claim 1.

3. A pharmaceutical composition made by mixing the salt of claim 1 and a pharmaceutically acceptable carrier.

4. A process for making a pharmaceutical composition comprising mixing the salt of claim 1 and a pharmaceutically acceptable carrier.

5. A method of treating a disorder selected from the group consisting of anxiety, substance abuse, and epilepsy, comprising administering to a subject in need thereof a therapeutically effective amount of the salt of claim 1.

6. A method of treating a disorder selected from the group consisting of anxiety, substance abuse, and epilepsy, comprising administering to a subject in need thereof a therapeutically effective amount of the composition of claim 2.

* * * * *

UNITED STATES PATENT AND TRADEMARK OFFICE
CERTIFICATE OF CORRECTION

PATENT NO. : 8,703,948 B2  
APPLICATION NO. : 11/939789  
DATED : April 22, 2014  
INVENTOR(S) : Steven J. Mehrman et al.

Page 1 of 1

It is certified that error appears in the above-identified patent and that said Letters Patent is hereby corrected as shown below:

Title page, column 1, item (75), line 5: "Francois Alexandre Lucas, Diest (BE)" should read
-- Francois Alexandre Lucas Hegyi, Diest (BE) --.

Signed and Sealed this
Sixth Day of January, 2015

Michelle K. Lee
*Deputy Director of the United States Patent and Trademark Office*